United States Patent
Marker

(10) Patent No.: US 7,868,214 B2
(45) Date of Patent: *Jan. 11, 2011

(54) PRODUCTION OF OLEFINS FROM BIORENEWABLE FEEDSTOCKS

(75) Inventor: Terry L. Marker, Palos Heights, IL (US)

(73) Assignee: UOP LLC, Des Plaines, IL (US)

( * ) Notice: Subject to any disclaimer, the term of this patent is extended or adjusted under 35 U.S.C. 154(b) by 614 days.

This patent is subject to a terminal disclaimer.

(21) Appl. No.: 11/876,940

(22) Filed: Oct. 23, 2007

(65) Prior Publication Data

US 2008/0035528 A1  Feb. 14, 2008

Related U.S. Application Data

(63) Continuation-in-part of application No. 11/432,012, filed on May 11, 2006, now Pat. No. 7,288,685.

(60) Provisional application No. 60/682,722, filed on May 19, 2005.

(51) Int. Cl.
*C10G 11/00* (2006.01)

(52) U.S. Cl. ............... 585/240; 585/241; 585/242; 208/67; 208/87; 208/90; 208/113; 208/179

(58) Field of Classification Search ......... 585/240–242; 208/67, 87, 90, 113, 179
See application file for complete search history.

(56) References Cited

U.S. PATENT DOCUMENTS

| | | | |
|---|---|---|---|
| 3,702,886 A | 11/1972 | Argauer et al. | 423/328 |
| 4,435,282 A * | 3/1984 | Bertolacini et al. | 208/113 |
| 5,504,259 A | 4/1996 | Diebold et al. | 568/697 |
| 6,538,169 B1 | 3/2003 | Pittman et al. | 585/653 |
| 7,288,685 B2 * | 10/2007 | Marker | 585/240 |

* cited by examiner

*Primary Examiner*—Robert J Hill, Jr.
*Assistant Examiner*—Brian McCaig
(74) *Attorney, Agent, or Firm*—Frank S. Molinaro

(57) ABSTRACT

A process for producing olefins from a feedstock comprising a petroleum and non-petroleum fraction has been developed. The process comprises first pretreating the feedstock to remove contaminants such as alkali metals and then cracking the purified feedstock in a fluidized catalytic cracking (FCC) zone operated at conditions to provide $C_2$-$C_5$ olefins. Alternatively, the non-petroleum fraction can first be treated and then mixed with petroleum fraction to provide the feedstock which is then catalytically cracked.

12 Claims, No Drawings

PRODUCTION OF OLEFINS FROM BIORENEWABLE FEEDSTOCKS

CROSS REFERENCE TO RELATED APPLICATIONS

This application is a Continuation-In-Part of application Ser. No. 11/432,012 filed May 11, 2006, now U.S Pat. No. 7,288,685, which in turn claims priority from Application Ser. No. 60/682,722 filed May 19, 2005 now abandoned, both of which are hereby incorporated by reference in their entirety.

FIELD OF THE INVENTION

This invention relates to a process for converting a feedstock comprising a petroleum and non-petroleum fraction to olefins. Examples of non-petroleum fractions are vegetable oils and used greases. The process involves first pre-treating the feedstock to remove contaminants such as alkali metals and then catalytically cracking the purified feedstock to provide a product stream comprising $C_2$-$C_5$ olefins.

BACKGROUND OF THE INVENTION

Fluid Catalytic Cracking (FCC) is one method which is used to produce olefins, especially propylene, from heavy crude fractions. There are reports in the literature that vegetable oils such as canola oil could be processed using FCC to give a hydrocarbon stream useful as a gasoline fuel.

Applicants have developed a process which successfully converts a feedstock comprising a petroleum and a non-petroleum fraction, e.g. vegetable oils and greases, to $C_2$-$C_5$ olefins. The process involves first removing contaminants such as alkali metals and then taking the purified feedstock, flowing it through an FCC zone and collecting a product stream comprising olefins.

SUMMARY OF THE INVENTION

One embodiment of the invention is a process for the catalytic cracking of a feedstock comprising a petroleum fraction and a non-petroleum fraction comprising first treating the feedstock in a pretreatment zone at pretreatment conditions to remove at least a portion of portion of contaminants present in the feedstock and produce an effluent stream; flowing the effluent from the pretreatment zone to a fluid catalytic cracking zone where the effluent is contacted with a cracking catalyst at cracking conditions to provide a product stream comprising $C_2$-$C_5$ olefins and hydrocarbons wherein the pretreatment step is selected from the group consisting of contacting the feedstock with an acidic ion exchange resin or contacting the feedstock with an acid solution.

In another embodiment, the non-petroleum fraction is first treated to remove contaminants and then mixed with the petroleum fraction to provide the feedstock.

This and other objects and embodiments will become clearer after the following detailed description of the invention.

DETAILED DESCRIPTION OF THE INVENTION

The feedstock which is used in the current process comprises a petroleum fraction and a non-petroleum fraction. The petroleum fraction can be any of those hydrocarbon streams which are routinely processed using fluidized catalytic cracking (FCC) technology and which are known in the art. The non-petroleum fraction includes fractions or feedstocks other than those obtained from crude oil. One example of a non-petroleum fraction is a biorenewable feedstock which comprise tri-glycerides and free fatty acids (FFA). Examples of these feedstocks include, but are not limited to, canola oil, corn oil, soy oils, rapeseed oil, soybean oil, colza oil, sunflower oil, hempseed oil, olive oil, linseed oil, coconut oil, castor oil, peanut oil, palm oil, mustard oil, cotton seed oil, inedible tallow, inedible oils, e.g. jatropha oil, yellow and brown greases, lard, train oil, fats in milk, fish oil, algal oil, tall oil, sewage sludge and the like. Tall oil is a by-product of the wood processing industry. Tall oil contains esters and rosin acids in addition to FFAs. Rosin acids are cyclic carboxylic acids. The triglycerides and FFAs of the typical vegetable or animal fat contain aliphatic hydrocarbon chains in their structure which have about 8 to about 24 carbon atoms. Pyrolysis oils, which are formed by the pyrolysis of cellulosic waste material can also be used as a non-petroleum feedstock or a portion of the feedstock. Other non-petroleum feedstock components include oxygenated liquids derived from gasification of coal or natural gas followed by a downstream liquefaction step such as Fischer-Tropsch technology or alcohol synthesis; oxygenated liquids derived from depolymerization, thermal or chemical, of waste plastics such as polypropylene, high density plastics such as polypropylene, high density polyethylene, and low density polyethylene; and other synthetic oils generated as byproducts from petrochemical and chemical processes. Mixtures of the above feedstocks may also be used.

However, these non-petroleum feedstocks also contain contaminants such as alkali metals, e.g. sodium and potassium, phosphorous as well as ash, water and detergents. Accordingly, the first step in the present invention is to remove as much of these contaminants as possible. One pretreatment step involves contacting the non-petroleum feedstock with an ion-exchange resin in a pretreatment zone at pretreatment conditions. The ion-exchange resin is an acidic ion exchange resin such as Amberlyst™-15 and can be used as a bed in a reactor through which the feedstock is flowed through, either upflow or downflow. The conditions at which the reactor is operated are well known in the art.

Another means for removing contaminants is a mild acid wash. This is carried out by contacting the feedstock with an acid such as sulfuric, acetic, nitric or hydrochloric acid in a reactor. The acid and feedstock can be contacted either in a batch or continuous process. Contacting is done with a dilute acid solution usually at ambient temperature and atmospheric pressure. If the contacting is done in a continuous manner, it is usually done in a counter current manner.

Yet another means of removing metal contaminants from the feedstock is through the use of guard beds which are well known in the art. These can include alumina guard beds either with or without demetallation catalysts such as nickel or cobalt.

Since only the non-petroleum fraction needs to be pretreated, the effluent from the pretreatment zone is now mixed with the petroleum fraction to provide a feedstock mixture which is now flowed to an FCC zone. Alternatively, the petroleum and non-petroleum fractions can be first mixed and then treated in a pretreatment zone as described above. Which method is used depends on the overall setup in any one refinery. In the FCC zone the hydrocarbonaceous components are cracked to olefins. Catalytic cracking is accomplished by contacting hydrocarbons in a reaction zone with a catalyst composed of finely divided particulate material. The reaction is catalytic cracking, as opposed to hydrocracking, and is carried out in the absence of added hydrogen or the consumption of hydrogen. As the cracking reaction proceeds, substantial amounts of coke are deposited on the catalyst. The catalyst is regenerated at high temperatures by burning coke from the catalyst in a regeneration zone. Coke-containing catalyst, Coke-containing catalyst, referred to herein as "coked catalyst", is continually transported from the reaction zone to the regeneration zone to be regenerated and replaced by essentially coke-free regenerated catalyst from the regeneration zone. Fluidization of the catalyst particles by various gaseous streams allows the transport of catalyst between the reaction zone and regeneration zone. Methods for cracking hydrocarbons in a fluidized stream of catalyst, transporting catalyst between reaction and regeneration zones, and combusting coke in the regenerator are well known by those skilled in the art of FCC processes.

An arrangement which can make up the FCC zone of the present invention is shown in U.S. Pat. No. 6,538,169 which is incorporated in its entirety by reference and comprises a separator vessel, a regenerator, a blending vessel and a vertical riser that provides a pneumatic conveyance zone in which conversion takes place. The catalysts which can be used in the present process are any of those well known in the art and comprises two components that may or may not be on the same matrix. The two components are circulated throughout the entire system. The first component may include any of the well-known catalysts that are used in the art of fluidized catalytic cracking, such as an active amorphous clay-type catalyst and/or a high activity, crystalline molecular sieve. Molecular sieve catalysts are preferred over amorphous catalysts because of their much-improved selectivity to desired products. Zeolites are the most commonly used molecular sieves in FCC processes. Preferably, the first catalyst component comprises a large pore zeolite, such as a Y-type zeolite, an active alumina material, a binder material, comprising either silica or alumina and an inert filler such as kaolin.

The zeolitic molecular sieves appropriate for the first catalyst component should have a large average pore size. Typically, molecular sieves with a large pore size have pores with openings of greater than 0.7 nm in effective diameter defined by greater than 10 and typically 12 membered rings. Pore Size Indices of large pores are above about 31. Suitable large pore zeolite components include synthetic zeolites such as X-type and Y-type zeolites, mordenite and faujasite. We have found that Y zeolites with low rare earth content are preferred in the first catalyst component. Low rare earth content denotes less than or equal to about 1.0 wt-% rare earth oxide on the zeolite portion of the catalyst. Octacat™ catalyst made by W.R. Grace & Co. is a suitable low rare earth Y-zeolite catalyst.

The second catalyst component comprises a catalyst containing, medium pore zeolites exemplified by ZSM-5, ZSM-11, ZSM-12, ZSM-23, ZSM-35, ZSM-38, ZSM-48, and other similar materials. U.S. Pat. No. 3,702,886 describes ZSM-5. Other suitable medium pore zeolites include ferrierite, erionite, and ST-5, developed by Petroleos de Venezuela, S.A. The second catalyst component preferably disperses the medium pore zeolite on a matrix comprising a binder material such as silica or alumina and an inert filler material such as kaolin. The second component may also comprise some other active material such as Beta zeolite. These catalyst compositions have a crystalline zeolite content of 10 to 25 wt-% or more and a matrix material content of 75 to 90 wt-%. Catalysts containing 25 wt-% crystalline zeolite material are preferred. Catalysts with greater crystalline zeolite content may be used, provided they have satisfactory attrition resistance. Medium pore zeolites are characterized by having an effective pore opening diameter of less than or equal to 0.7 nm, rings of 10 or fewer members and a Pore Size Index of less than 31.

The total catalyst composition should contain 1 to 10 wt-% of a medium pore zeolite with greater than or equal to 1.75 wt-% being preferred. When the second catalyst component contains 25 wt-% crystalline zeolite, the composition contains 4 to 40 wt-% of the second catalyst component with a preferred content of greater than or equal to 7 wt-%. ZSM-5 and ST-5 type zeolites are particularly preferred since their high coke resistivity will tend to preserve active cracking sites as the catalyst composition makes multiple passes through the riser, thereby maintaining overall activity. The first catalyst component will comprise the balance of the catalyst composition. The relative proportions of the first and second components in the catalyst composition will not substantially vary throughout the FCC unit.

The high concentration of the medium pore zeolite in the second component of the catalyst composition improves selectivity to light olefins by further cracking the lighter naphtha range molecules. But at the same time, the resulting smaller concentration of the first catalyst component still exhibits sufficient activity to maintain conversion of the heavier feed molecules to a reasonably high level.

Cracking of the feedstock takes place in the riser section of the FCC zone. Feed is introduced into the riser by a nozzle resulting in the rapid vaporization of the feed. Before contacting the catalyst, the feed will ordinarily have a temperature of about 149° C. to about 316° C. (300° F. to 600° F.). The catalyst is flowed from a blending vessel to the riser where it contacts the contacts the feed for a time of about 2 seconds or less.

The blended catalyst and reacted feed vapors are then discharged from the top of the riser through an outlet and separated into a cracked product vapor stream including olefins and a collection of catalyst particles covered with substantial quantities of coke and generally referred to as "coked catalyst." In an effort to minimize the contact time of the feed and the catalyst which may promote further conversion of desired products to undesirable other products, any arrangement of separators such as a swirl arm arrangement can be used to remove coked catalyst from the product stream quickly. The separator, e.g. swirl arm separator, is located in an upper portion of a chamber with a stripping zone situated in the lower portion of the chamber. Catalyst separated by the swirl arm arrangement drops down into the stripping zone. The cracked product vapor stream comprising cracked hydrocarbons including light olefins and some catalyst exit the chamber via a conduit which is in communication with cyclones. The cyclones remove remaining catalyst particles from the product vapor stream to reduce particle concentrations to very low levels. The product vapor stream then exits the top of the separating vessel. Catalyst separated by the cyclones is returned to the separating vessel and then to the stripping zone. The stripping zone removes adsorbed hydrocarbons from the surface of the catalyst by counter-current contact with steam.

A first portion of the coked catalyst is recycled to the riser without first undergoing regeneration. A second portion of the coked catalyst is regenerated in the regenerator before it is delivered to the riser. The first and second portions of the catalyst may be blended in a blending vessel before introduction to the riser. The recycled catalyst portion may be withdrawn from the stripping zone for transfer to the blending vessel.

The second portion of the coked, stripped catalyst is transported to the regeneration zone. In the regeneration zone the coked catalyst undergoes regeneration by combustion of coke on the surface of the catalyst particles by contact with an oxygen-containing gas. The oxygen-containing gas enters the bottom of the regenerator and passes through a dense fluidizing bed of catalyst. Flue gas consisting primarily of $CO_2$ and perhaps containing CO passes upwardly from the dense bed into a dilute phase of the regenerator. A separator, such as cyclones or other means, remove entrained catalyst particles from the rising flue gas before the flue gas exits the vessel through an outlet. Combustion of coke from the catalyst particles raises the temperatures of the catalyst which is withdrawn from the regenerator and flowed to a blending vessel. Fluidizing gas Fluidizing gas passed into the blending vessel contacts the catalyst and maintains the catalyst in a fluidized state to blend the recycled and regenerated catalyst.

The regenerated catalyst which is relatively hot is cooled by the unregenerated, coked catalyst which is relatively cool to reduce the temperature of the regenerated catalyst by 28° to 83° C. (50° to 150° F.) depending upon the regenerator temperature and the coked catalyst recycle rate. The ratio of recycled catalyst to regenerated catalyst entering the blending zone will be in a broad range from about 0.1 to about 5.0 and more typically in a range from about 0.3 to about 3.0. Preferably, the blended catalyst will comprise a 1:1 ratio of recycled catalyst to regenerated catalyst.

Regenerated catalyst from the regenerator will usually have a temperature in a range from about 677° to about 760° C. (1250° to 1400° F.) and, more typically, from about 699° to about 760° C. (1290° to 1400° F.). The temperature of the recycled catalyst portion will usually be in a range from about 510° to about 621° C. (950° to 1150° F.). The relative proportions of the recycled and regenerated catalyst will determine the temperature of the blended catalyst mixture that enters the riser. The blended catalyst mixture will usually range from about 593° to about 704° C. (1100° to 1300° F.).

Low hydrocarbon partial pressure operates to favor the production of light olefins. Accordingly, the riser pressure is set at about 172 to 241 kPa (25 to 35 psia) with a hydrocarbon partial pressure of about 35 to 172 kPa (5 to 25 psia), with a preferred hydrocarbon partial pressure of about 69 to 138 kPa (10 to 20 psia). This relatively low partial pressure for hydrocarbon is achieved by using steam as a diluent to the extent that the diluent is 10 to 55 wt-% of feed and preferably about 15 wt-% of feed. Other diluents such as dry gas can be used to reach equivalent hydrocarbon partial pressures.

The temperature of the cracked stream at the riser outlet will be about 510° to 621° C. (950° to 1150° F.). However, we have found that riser outlet temperatures above 566° C. (1050° F.) make more dry gas and more olefins. Whereas, riser outlet temperatures below 566° C. (1050° F.) make less ethylene and propylene. Accordingly, it is preferred to run the FCC process at a preferred temperature of about 566° C. to about 630° C., preferred pressure of about 138 kPa to about 240 kPa (20 to 35 psia). Another condition for the process is the catalyst to oil ratio which can vary from about 5 to about 20 and preferably from about 10 to about 15.

Although, as stated, the feed is normally introduced into the riser section of the FCC zone, it is also within the scope of the present invention that the effluent from the pre-treatment zone is introduced into the lift section of the FCC reactor. The temperature in the lift section will be very hot and range from about 700° C. (1292° F.) to about 760° C. (1400° F.) with a catalyst to oil ratio of about 100 to about 150. It is anticipated that introducing the oil feed into the lift section will produce considerable amounts of propylene and ethylene.

The following examples are presented in illustration of this invention and are not intended as undue limitations on the generally broad scope of the invention as set out in the appended claims.

EXAMPLE

Catalytic cracking of soybean oil was tested using an advanced cracking evaluation pilot plant. A commercial fluid catalytic catalyst from W.R. Grace, Inc. was used. The soybean oil was obtained from Aldrich Chemical Co. and the gas and liquid hydrocarbon products were analyzed by gas chromatography. The analyses did not include oxygen balance nor water analysis. The reaction was run at 538° C. (1000° F.) at a catalyst:oil ratio of 3:1 and a WHSV $(hr^{-1})$ of 3 $hr^{-1}$.

Based on these data, calculations were carried out to determine conversion at more severe conditions which are a temperature of 565° C. (1050° F.), a catalyst:oil ratio of 10/1 and 10% steam.

The actual and calculated conversions are presented below.

| Actual and Calculated Cracking Conversions for Soybean Oil | | |
|---|---|---|
| Component | Actual (%) | Calculated (%) |
| C2 & Methane | 1.9 | 12.8 |
| C3 | 5.4 | 24.5 |
| C4 | 6.6 | 13.5 |
| gasoline | 45.4 | 23.0 |
| LCO[1] | 11.4 | 5.0 |
| CSO[2] | 13.1 | 3.0 |
| coke | 4.5 | 6.5 |
| water | 11.7 (estimate) | 11.7 |

[1]LCO is light cycle oil which boils between 220-343° C.
[2]CSO is clarified slurry oil which boils between 343 and 538° C.

The invention claimed is:

1. A process for the catalytic cracking of a feedstock comprising a petroleum fraction and a non-petroleum fraction comprising first treating the feedstock in a pretreatment zone at pretreatment conditions to remove at least a portion of contaminants present in the feedstock and produce an effluent stream; flowing the effluent from the pretreatment zone to a fluid catalytic cracking zone where the effluent is contacted with a cracking catalyst at cracking conditions to provide a product stream comprising $C_2$-$C_5$ olefins and hydrocarbons wherein the pretreatment step is selected from the group consisting of contacting the feedstock with an acidic ion exchange resin or contacting the feedstock with an acid solution.

2. The process of claim 1 where the cracking conditions include a temperature of about 566° C. (1050° F.) to about 630° C. (1166° F.), a pressure of about 138 kPa (20 psia) to about 240 kPa (35 psia) and a catalyst to oil ratio of about 5 to about 20.

3. The process of claim 1 where the effluent is injected into the lift section of the fluid catalytic cracking zone.

4. The process of claim 3 where the temperature in the lift section varies from about 700° C. (1292° F.) to about 760° C. (1400° F.).

5. The process of claim 1 wherein the non-petroleum fraction is selected from the group consisting of canola oil, corn oil, soy oil, rapeseed oil, soybean oil, colza oil, tall oil, sunflower oil, hempseed oil, olive oil, linseed oil, coconut oil, castor oil, peanut oil, palm oil, mustard oil, cottonseed oil, inedible oils, inedible tallow, yellow and brown greases, lard, train oil, fats in milk, fish oil, algal oil, sewage sludge, pyrolysis oil, oxygenated liquids derived from the gasification of coal, oxygenated liquids derived from depolymerization, synthetic oils, and mixtures thereof.

6. The process of claim 5 where the inedible oil is jatropha oil.

7. A process for the catalytic cracking of a feedstock comprising a petroleum fraction and a non-petroleum fraction comprising first treating the non-petroleum fraction in a pretreatment zone at pretreatment conditions to remove at least a portion of contaminants present in the non-petroleum fraction and produce a purified non-petroleum stream; mixing the purified non-petroleum stream with a petroleum fraction to provide a feedstock; flowing the feedstock to a fluid catalytic cracking zone where the feedstock is contacted with a cracking catalyst at cracking catalyst at cracking conditions to provide a product stream comprising $C_2$-$C_5$ olefins and hydrocarbons; wherein the pretreatment step is selected from the group consisting of contacting the non-petroleum fraction with an acidic ion exchange resin or contacting the non-petroleum fraction with an acid solution.

8. The process of claim 7 where the cracking conditions include a temperature of about 566° C. (1050° F.) to about 630° C. (1166° F.), a pressure of about 138 kPa (20 psia) to about 240 kPa (35 psia) and a catalyst to oil ratio of about 5 to about 20.

9. The process of claim 7 where the effluent is injected into the lift section of the fluid catalytic cracking zone.

10. The process of claim 9 where the temperature in the lift section varies from about 700° C. (1292° F.) to about 760° C. (1400° F.).

11. The process of claim 7 wherein the non-petroleum fraction is selected from the group consisting of canola oil, corn oil, soy oil, rapeseed oil, soybean oil, colza oil, tall oil, sunflower oil, hempseed oil, olive oil, linseed oil, coconut oil, castor oil, peanut oil, palm oil, mustard oil, cottonseed oil, inedible oils, inedible tallow, yellow and brown greases, lard, train oil, fats in milk, fish oil, algal oil, sewage sludge, pyrolysis oil, oxygenated liquids derived from the gasification of coal, oxygenated liquids derived from depolymerization, synthetic oils, and mixtures thereof.

12. The process of claim 11 where the inedible oil is jatropha oil.

\* \* \* \* \*